United States Patent
O'Lenick, Jr.

[11] Patent Number: 5,929,268
[45] Date of Patent: Jul. 27, 1999

[54] SILICONE LACTYLATES

[75] Inventor: Anthony J. O'Lenick, Jr., Dacula, Ga.

[73] Assignee: Lambent Technologies Inc, Norcross, Ga.

[21] Appl. No.: 09/189,181

[22] Filed: Nov. 10, 1998

[51] Int. Cl.[6] .................... C07F 7/08; C07F 7/18
[52] U.S. Cl. ............................................. 556/437
[58] Field of Search ............................................. 556/437

[56] References Cited

U.S. PATENT DOCUMENTS

| | | | |
|---|---|---|---|
| 4,146,548 | 3/1979 | Forsythe . | |
| 5,248,783 | 9/1993 | O'Lenick | 548/110 |
| 5,296,625 | 3/1994 | O'Lenick, Jr. et al. | 556/437 |
| 5,374,759 | 12/1994 | Imperante et al. | 556/437 |

*Primary Examiner*—Paul F. Shaver

[57] ABSTRACT

The invention relates to a series of novel silicone based lactylates. This class of compounds provides unique emulsification properties as well as outstanding wet comb and conditioning properties when applied to hair. The compounds of the present invention are prepared by reacting a the carboxyl group on a silicone polymer with the hydroxyl group in lactic acid.

7 Claims, No Drawings

SILICONE LACTYLATES

BACKGROUND OF THE INVENTION

1. Field of the Invention

The present invention relates to a series of novel silicone based lactylates. This class of compounds provides unique emulsification properties as well as wetcomb and conditioning properties when applied on hair. The compounds of the present invention are prepared by reacting a the carboxyl group on a silicone polymer with the hydroxyl group in lactic acid.

2. Arts and Practices

Silicone compounds have been known to be active at the surface of cellulosic and synthetic fibers as well as paper. They are good nondurable lubricants but are water insoluble.

Fatty lactylates are also known. U.S. Pat. No. 3,883,669 to Tsen et al, teaches the method of making lactylate salts. The methodology includes a reaction of fatty acid with lactic acid. The methodology is directed toward fatty derived materials. The present invention is aimed at making silicone based materials that provide not only the emulsification properties, but also provide conditioning and softening properties to hair. These properties are lacking in traditional lactylates.

U.S. Pat. No. 4,146,548 to Forsythe, incorporated herein by reference, describes an improved method of preparation of lactylates.

The beneficial aspects of making silicone lactylates on wet comb properties in shampoos and softening properties of the silicone make the compounds of the present invention unique.

THE INVENTION

Object of the Invention

It is the object of the present invention to provide novel silicone lactylates and shampoo compositions containing them. These compounds in shampoos provide outstanding emulsification properties of oils like silicone oil and outstanding wet comb when applied to hair.

It is another objective of the current invention to provide silicone lactylate which can be used in personal care to provide superior wet comb and softening properties when applied to hair.

SUMMARY OF THE INVENTION

The present invention relates to novel silicone lactylates. The compounds have a unique combination of properties due to thier unique structure. The silicone group, lactate group and alkoxylate group render the compounds of the present invention highly lubricious to the hair, soluble in water, and outstanding emulsifiers. To obtain this combination of properties, all three components need to be present.

Silicone carboxylates are raw materials for preparation of the compounds of the present invention. They are the topic of U.S. Pat. No. 5,296,625 issued March 1994 to O'Lenick, et al.

These materials are reacted with lactic acid to make the lactylate of the present invention. The carboxylates dfo not exhibit all of the desired properties of the lactylates.

Silicone carboxylates a raw material in the preparation of the present invention are prepared by the reaction of an anhydride with an hydroxy silicone polymer. Suitable anhydrides for the preparation of the compounds of the present invention are cyclic anhydrides, which react easily at mild conditions with the silicone hydroxyl group to produce an ester carboxylate. Typical of the reaction is the following sequence utilizing succinic anhydride;

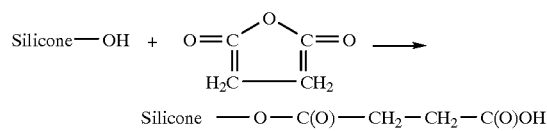

The silicone —OH represents the hydroxyl group on the silicone polymer described elsewhere in the disclosure.

The compounds of this invention are the reaction of the above carboxylate with lactic acid. Lactic acid is a hydroxy acid conforming to the following structure;

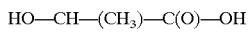

The reaction is as follows:

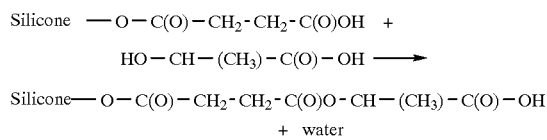

Silicone ester carboxylates of U.S. Pat. No. 5,296,625 are made by the reaction of an anhydride and a hydroxy containing silicone compound. The compounds of the '625 invention conform to the following structure;

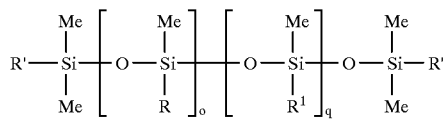

wherein;

Me is methyl;

R and R' are $CH_3$ or $$—(CH_2)_3—O—(EO)_a\text{-}(PO)_b\text{-}(EO)_c\text{-}C(O)—R''—C(O)—OH;$$

with the proviso that both R and R' are not $CH_3$;

R" is selected from $—CH_2—CH_2—$; $—CH=CH—$; $—CH_2—C(R^7)—H$;

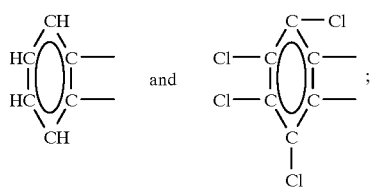

$R^7$ is alkyl having from 1 to 20 carbon atoms;
$R^1$ is selected from lower alkyl $CH_3(CH)_n$- or phenyl;
n is an integer from 0 to 8;
a, b and c are integers independently ranging from 0 to 20;
EO is an ethylene oxide residue —$(CH_2CH_2$—O)—;
PO is a propylene oxide residue —$(CH_2CH(CH_3)$—O)—;
o is an integer ranging from 1 to 100;
q is an integer ranging from 0 to 500.

Compounds of the present invention conform to the following structure;

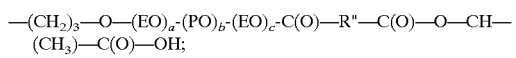

wherein;

Me is methyl;

R and R' are selected from methyl and

—$(CH_2)_3$—O—$(EO)_a$-$(PO)_b$-$(EO)_c$-C(O)—R"—C(O)—O—CH—$(CH_3)$—C(O)—OH;

with the proviso that both R and R' are not methyl;

R" is selected from —$CH_2$—$CH_2$—; —$CH_2$—$C(R^7)$—H;

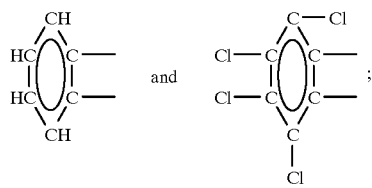

$R^7$ is alkyl having from 1 to 20 carbon atoms;
$R^1$ is selected from lower alkyl $CH_3(CH)_n$- or phenyl;
n is an integer from 0 to 8;
a, b and c are integers independently ranging from 0 to 20;
EO is an ethylene oxide residue —$(CH_2CH_2$—O)—;
PO is a propylene oxide residue —$(CH_2CH(CH_3)$—O)—;
o is an integer ranging from 1 to 100;
q is an integer ranging from 0 to 500.

Preferred Embodiment

In a preferred embodiment R" is —$CH_2$—$CH_2$—.

In a preferred embodiment R" is —$CH_2$—$C(R^7)$—H.

In another preferred embodiment R" is

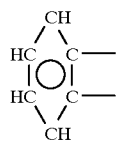

In another preferred embodiment R" is

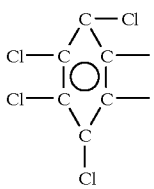

In a preferred embodiment $R^7$ is alkyl having from 6 to 20 carbon atoms.

In a preferred embodiment $R^7$ is alkyl having from 12 to 20 carbon atoms.

In a preferred embodiment R' is methyl.

RAW MATERIAL EXAMPLES

The raw material compounds for the present invention are prepared by the reaction of a hydroxy silicone compound and an anhydride. Examples of suitable reactants are as follows;

REACTANTS

Anhydrides

The various anhydrides listed are all items of commerce and are prepared by methods known to those skilled in the art.

Reactant Example I (Succinic Anhydride)

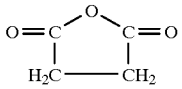

Reactant Example II (Alkyl Succinic Anhydride)

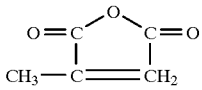

Reactant Example III (Alkyl Succinic Anhydride)

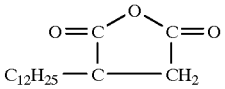

Reactant Example IV (Alkyl Succinic Anhydride)

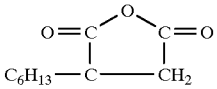

Reactant Example V (Alkyl Succinic Anhydride)

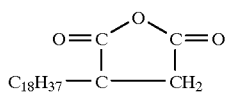

Reactant Example VI (Alkyl Succinic Anhydride)

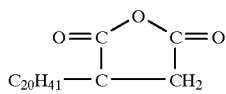

Reactant Example VII ( Maleic Anhydride)

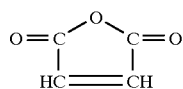

Reactant Example VIII (Phthalic Anhydride)

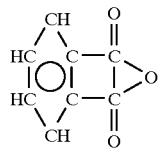

Reactant Example IX (Tetrachlorophthalic Anhydride)

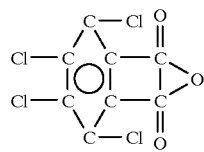

Hydroxy Silicone Compounds

Many manufacturers offer a series of hydroxy silicone compounds suitable for use as raw materials in the preparation of the esters of the present invention. These materials are marketed under the many trade names. Siltech Inc, Union Carbide, Dow Corning, Mazer and many other manufacturers also offer the compounds commercially.

The preferred method of placing this type of reactive hydroxyl group into the silicone polymer is by the reaction of silanic hydrogen containing polymer with allyl alcohol alkoxylates. This technology is well known to those skilled in the art and are described in U.S. Pat. No. 4,083,856. These hydroxyl functional silicone compounds are subsequently reacted with anhydrides, to make the compounds of the present invention.

Additionally, hydroxy silicone compounds are available from Siltech Inc. Norcross Ga. These compounds conform to the following generic structure;

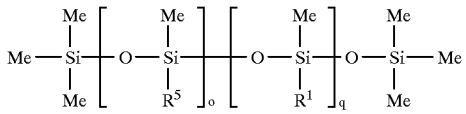

wherein;

Me is methyl;

$R^5$ is —$(CH_2)_3$—O—$(EO)_a$-$(PO)_b$-$(EO)_c$-H $R^1$ is selected from lower alkyl $CH_3(CH)_n$- or phenyl;

n is an integer from 0 to 8;

a, b and c are integers independently ranging from 0 to 20;

EO is an ethylene oxide residue —$(CH_2CH_2$—O)—;

PO is a propylene oxide residue —$(CH_2CH(CH_3)$—O)—;

o is an integer ranging from 1 to 100;

q is an integer ranging from 0 to 500.

| Example | Name | a | b | c | o | q |
|---|---|---|---|---|---|---|
| 1 | Siltech H 1000 | 3 | 0 | 0 | 2 | 54 |
| 2 | Siltech H 1100 | 10 | 5 | 10 | 10 | 100 |
| 3 | Siltech H 1200 | 20 | 20 | 20 | 2 | 56 |
| 4 | Siltech H 1300 | 10 | 10 | 10 | 6 | 26 |
| 5 | Siltech H 1400 | 0 | 10 | 0 | 4 | 200 |
| 6 | Siltech H 1500 | 5 | 5 | 5 | 2 | 50 |
| 7 | Siltech H 1600 | 0 | 6 | 0 | 10 | 25 |
| 8 | Siltech H 1700 | 0 | 0 | 0 | 5 | 10 |

Terminal Substituted Dimethicone Copolyol Compounds

Terminal substituted dimethicone copolyol compounds are well known and are marketed in the trade under many names.

The preferred method of placing this type of reactive hydoxyl group into the silicone polymer is by the reaction of terminal silanic hydrogen containing polymer with allyl alcohol alkoxylates. This technology is well known to those skilled in the art and are described in U.S. Pat. No. 4,083,856.

These materials are available from Siltech Inc. Norcross Ga. and are marketed under the Siltech T series trade name.

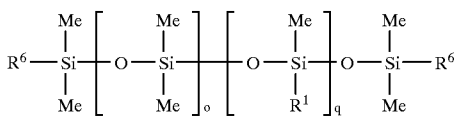

wherein;

Me is methyl;

$R^6$ is —$(CH_2)_3$—O—$(EO)_a$-$(PO)_b$-$(EO)_c$-H $R^1$ is selected from lower alkyl $CH_3(CH)_n$- or phenyl;

n is an integer from 0 to 8;

a, b and c are integers independently ranging from 0 to 20;

EO is an ethylene oxide residue —$(CH_2CH_2$—O)—;

PO is a propylene oxide residue —$(CH_2CH(CH_3)$—O)—;

o is an integer ranging from 1 to 100;
q is an integer ranging from 0 to 500.

| Example | Name | a | b | c | Equivalent Molecular Weight |
|---|---|---|---|---|---|
| 9 | Siltech T 701 | 0 | 0 | 0 | 1,000 |
| 10 | Siltech T 706 | 5 | 1 | 0 | 6,000 |
| 11 | Siltech T 710 | 2 | 1 | 1 | 10,000 |
| 12 | Siltech T 750 | 10 | 5 | 10 | 50,000 |
| 13 | Siltech T 790 | 20 | 20 | 20 | 86,000 |

General Reaction Conditions

The reaction can be run with either a stiochiometric amount of the anhydride, or an excess of silicone polymer.

Into a suitable round bottom, three neck flask equipped with a thermometer and a nitrogen sparge is added the specified number of grams of the specified silicone compound and the specified number of grams of the specified anhydride. The reaction mass is blanketed with nitrogen, and heated to 80 and 110 C. under the inert nitrogen blanket. Within four to five hours the theoretical acid value is obtained. The product is a clear liquid and is used without additional purification.

Example 14

Into a suitable round bottom, three neck flask equipped with a thermometer and a nitrogen sparge is added number 100.0 grams of silicone example 1 and the 1,000.0 grams of succinic anhydride. The reaction mass is then blanketed with nitrogen and heated to 80 and 110 C. This temperature is maintained for four to five hours. The theoretical acid value is obtained. The product is a clear liquid and is used without additional purification.

Examples 15–32

Example 14 is repeated only this time substituting the specified number of grams of the anhydride specified and the specified type and number of grams of silicone compound as shown below;

| | Anhydride | | | |
|---|---|---|---|---|
| | Reactant | | Silicone Compound | |
| Example | Example | Grams | Example | Grams |
| 15 | I | 100.0 | 1 | 2,329.0 |
| 16 | II | 115.0 | 2 | 2,032.0 |
| 17 | III | 269.0 | 3 | 5,129.0 |
| 18 | IV | 185.0 | 4 | 347.6 |
| 19 | V | 316.0 | 5 | 4,407.0 |
| 20 | VI | 340.0 | 6 | 2,743.0 |
| 21 | VII | 98.0 | 7 | 3,550.8 |
| 22 | VIII | 148.0 | 8 | 1,512.4 |
| 23 | IX | 288.0 | 9 | 1,000.0 |
| 24 | I | 100.0 | 10 | 6,000.0 |
| 25 | II | 115.0 | 11 | 10,000.0 |
| 26 | III | 269.0 | 12 | 50,000.0 |
| 27 | IV | 185.0 | 13 | 86,000.0 |
| 28 | V | 316.0 | 1 | 2,329.0 |
| 29 | VI | 340.0 | 2 | 2,032.0 |
| 30 | VII | 98.0 | 3 | 5,129.0 |
| 31 | VIII | 148.0 | 4 | 347.6 |
| 32 | IX | 288.0 | 5 | 4,407.0 |

COMPOUNDS OF THE PRESENT INVENTION

Compounds of the present invention are prepared by the esterification reaction of lactic acid and a carboxy silicone.

General Procedure

The esterification reaction is carride out by placing the required amount of the specified carboxy silicone into a suitable flask. Next is added 82.0 grams of lactic acid is added. The reaction can be carried out with out without catalyst. However catalysty is recommended to speed up the reaction. The catalysts of choice are para touluene sulfonic acid, sulfuric acid and tin salts. We recommend 0.1% by weight of dibutyl tin dilaurate. The reaction mass is heated to 180–200° C. Water is distilled off. When 97% of the theoretical amount of water is distilled off, the reaction is stopped. The product is used without purification.

| | Raw Material | |
|---|---|---|
| Example | Example | Grams |
| 33 | 15 | 2,429.0 |
| 34 | 16 | 2,147.0 |
| 35 | 17 | 5,398.0 |
| 36 | 18 | 532.6 |
| 37 | 19 | 4,723.0 |
| 38 | 20 | 3,083.0 |
| 39 | 21 | 3,648.0 |
| 40 | 22 | 1,660.4 |
| 41 | 23 | 1,288.0 |
| 42 | 24 | 6,100.0 |
| 43 | 25 | 10,115.0 |
| 44 | 26 | 50,269.0 |
| 45 | 27 | 86,185.0 |
| 46 | 28 | 2,645.0 |
| 47 | 29 | 2,372.0 |
| 48 | 30 | 5,227.0 |
| 49 | 31 | 495.6 |
| 50 | 32 | 4,695.0 |

The silicone group, lactate group and alkoxylate group render the compounds of the present invention highly lubricious to the hair, soluble in water, and outstanding emulsifiers. To obtain this combination of properties, all three components need to be present.

The compounds of the present invention are used in personal care applications like shampoos.

What is claimed:

1. A silicone compound conforming to the following structure;

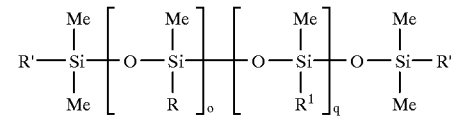

wherein;

Me is methyl;

R and R' are selected from methyl and

—(CH$_2$)$_3$—O—(EO)$_a$-(PO)$_b$-(EO)$_c$-C(O)—R"—C(O)O—CH—(CH$_3$)—C(O)—OH;

with the proviso that both R and R' are not methyl;

R" is selected from —CH$_2$—CH$_2$—; —CH$_2$—C(R$^7$)—H;

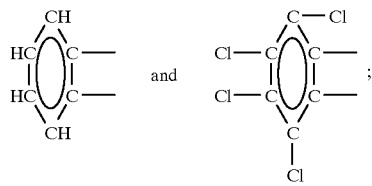

R$^7$ is alkyl having from 1 to 20 carbon atoms;
R$^1$ is selected from lower alkyl CH$_3$(CH)$_n$- or phenyl;
n is an integer from 0 to 8;
a, b and c are integers independently ranging from 0 to 20;
EO is an ethylene oxide residue —(CH$_2$CH$_2$—O)—;
PO is a propylene oxide residue —(CH$_2$CH(CH$_3$)—O)—;
o is an integer ranging from 1 to 100;
q is an integer ranging from 0 to 500.

2. A compound of claim 1 wherein R" is —CH$_2$—CH$_2$—.

3. A compound of claim 1 wherein R" is —CH$_2$—C(R$^7$)—H.

4. A compound of claim 1 wherein R" is

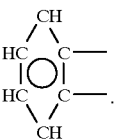

5. A compound of claim 1 wherein R" is

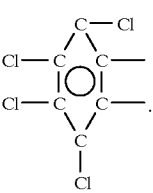

6. A compound of claim 3 wherein R$^7$ is alkyl having from 6 to 2 carbon atoms.

7. A compound of claim 3 wherein R$^7$ is alkyl having from 12 to 20 carbon atoms.

* * * * *